(12) United States Patent
Tadiparthi et al.

(10) Patent No.: US 9,604,986 B2
(45) Date of Patent: Mar. 28, 2017

(54) POLYMORPHS AND PROCESS FOR PREPARATION OF (2S, 5R)-7-OXO-N-[(2S)-PYRROLIDIN-2-YL-METHYLOXY]-6-(SULFOOXY)-1,6-DIAZABICYCLO[3.2.1]OCTANE-2-CARBOXAMIDE

(71) Applicant: WOCKHARDT LIMITED, Aurangabad (IN)

(72) Inventors: Ravikumar Tadiparthi, Aurangabad (IN); Bharat Dond, Aurangabad (IN); Satish Birajdar, Latur (IN); Amol Kale, Aurangabad (IN); Vijaykumar Jagdishwar Patil, Solapur (IN)

(73) Assignee: WOCKHARDT LIMITED, Aurangabad (IN)

( * ) Notice: Subject to any disclaimer, the term of this patent is extended or adjusted under 35 U.S.C. 154(b) by 0 days.

(21) Appl. No.: 15/038,452

(22) PCT Filed: Jul. 8, 2014

(86) PCT No.: PCT/IB2014/062942
§ 371 (c)(1),
(2) Date: May 21, 2016

(87) PCT Pub. No.: WO2015/079329
PCT Pub. Date: Jun. 4, 2015

(65) Prior Publication Data
US 2016/0289231 A1 Oct. 6, 2016

(30) Foreign Application Priority Data

Nov. 26, 2013 (IN) .......................... 3705/MUM/2013
Apr. 18, 2014 (IN) .......................... 1406/MUM/2014

(51) Int. Cl.
*C07D 515/02* (2006.01)
*C07D 471/08* (2006.01)

(52) U.S. Cl.
CPC ................. *C07D 471/08* (2013.01)

(58) Field of Classification Search
CPC .................................................... C07D 471/08
(Continued)

(56) References Cited

U.S. PATENT DOCUMENTS

2013/0225554 A1 8/2013 Maiti et al.
2015/0203503 A1* 7/2015 Patil .................... C07D 471/08
514/2.4

FOREIGN PATENT DOCUMENTS

WO WO/2009/091856 7/2009
WO WO2014033560 A1 3/2014

OTHER PUBLICATIONS

Hanessian et al., Optimization of the catalytic asymmetric addition of nitroalkanes to cyclic enones with trans-4,5-methano-L-proline. Org Lett. Oct. 12, 2006;8(21):4787-4790.

* cited by examiner

*Primary Examiner* — T. Victor Oh
(74) *Attorney, Agent, or Firm* — Bio Intellectual Property Services LLC (Bio IPS); O. (Sam) Zaghmout (57) ABSTRACT

A process for preparation of compound of Formula (I) is disclosed. The application is also directed to polymorphic forms of the compound of formula (I).

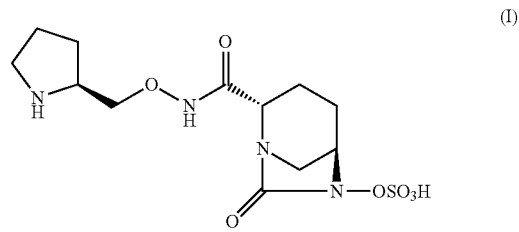

8 Claims, 2 Drawing Sheets

POLYMORPHS AND PROCESS FOR PREPARATION OF (2S, 5R)-7-OXO-N-[(2S)-PYRROLIDIN-2-YL-METHYLOXY]-6-(SULFOOXY)-1,6-DIAZABICYCLO[3.2.1]OCTANE-2-CARBOXAMIDE

RELATED APPLICATIONS

This application claims priority to Indian Provisional Patent Application Nos. 3705/MUM/2013 filed Nov. 26, 2013; and 1406/MUM/2014 filed Apr. 18, 2014, all of which are incorporated herein by reference in their entirety.

FIELD OF THE INVENTION

The invention relates to a process for preparation of (2S, 5R)-7-oxo-N-[(2S)-pyrrolidin-2-yl-methyloxy]-6-(sulfooxy)-1,6-diazabicyclo[3.2.1]octane-2-carboxamide. The invention also relates to substantially pure (2S, 5R)-7-oxo-N-[(2S)-pyrrolidin-2-yl-methyloxy]-6-(sulfooxy)-1,6-diazabicyclo [3.2.1]octane-2-carboxamide and process for its preparation.

BACKGROUND OF INVENTION

A compound of Formula (I), chemically known as (2S, 5R)-7-oxo-N-[(2S)-pyrrolidin-2-yl-methyloxy]-6-(sulfooxy)-1,6-diazabicyclo[3.2.1]octane-2-carboxamide has antibacterial properties and is disclosed in PCT International Patent Application No. PCT/IB2013/053092.

Formula (I)

SUMMARY OF THE INVENTION

In one general aspect, there is provided a process for preparation of a compound of Formula (I), comprising:

Formula (I)

(a) reacting a compound of Formula (II) with a compound of Formula (III) to obtain a compound of Formula (IV);

Formula (II)

Formula (III)

Formula (IV)

(b) hydrogenolysis of a compound of Formula (IV) to obtain a compound of Formula (V);

Formula (V)

(c) converting a compound of Formula (V) to obtain a compound of Formula (VI); and Formula (VI)

(d) converting a compound of Formula (VI) to obtain a compound of Formula (I).

In another general aspect, there is provided a substantially pure (2S, 5R)-7-oxo-N-[(2S)-pyrrolidin-2-yl-methyloxy]-6-(sulfooxy)-1,6-diazabicyclo[3.2.1]octane-2-carboxamide and process for its preparation.

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The term "OBn" as used herein refers to benzyloxy.
The term "EDC" as used herein refers to 1-ethyl-3-(3-dimethylamino propyl)carbodiimide.
The term "HOBt" as used herein refers to 1-hydroxybenzotriazole.
The term "TBAA" as used herein refers to tetrabutyl ammonium acetate.
The term "pharmaceutically acceptable derivative" as used herein refers to and includes any pharmaceutically acceptable salt, pro-drugs, metabolites, esters, ethers, hydrates, polymorphs, solvates, complexes, enantiomers or adducts of a compound described herein which, upon administration to a subject, is capable of providing (directly or indirectly) the parent compound. For example, the term "antibacterial or a pharmaceutically acceptable derivative thereof" includes all derivatives of the antibacterial agent (such as salt, prodrugs, metabolites, esters, ethers, hydrates, polymorphs, solvates, complexes, enantiomers or adducts) which, upon administration to a subject, is capable of providing (directly or indirectly) the antibacterial compound.

In one general aspect, there is provided a process for preparation of a compound of Formula (I), comprising:

Formula (I)

(a) reacting a compound of Formula (II) with a compound of Formula (III) to obtain a compound of Formula (IV);

Formula (II)

Formula (III)

Formula (IV)

(b) hydrogenolysis of a compound of Formula (IV) to obtain a compound of Formula (V);

Formula (V)

(c) converting a compound of Formula (V) to obtain a compound of Formula (VI); and Formula (VI)

(d) converting a compound of Formula (VI) to obtain a compound of Formula (I)

The compound of Formula (IV) is obtained by reacting a compound of Formula (II) with a compound of Formula (III). In some embodiments, this reaction is carried out in presence of 1-hydroxybenzotriazole. In some other embodiments, the compound of Formula (IV) is obtained by reacting a compound of Formula (II) with a compound of Formula (III) in presence of 1-hydroxybenzotriazole and 1-ethyl-3-(3-dimethylaminopropyl)carbodiimide hydrochloride. In some embodiments, this reaction is carried out in a mixture of water and dimethylformamide (DMF) as reaction solvent.

The compound of Formula (V) is obtained by hydrogenolysis of a compound of a compound of Formula (IV). The hydrogenolysis reaction can be carried out using a suitable hydrogenolysis agent. In some embodiments, hydrogenolysis of a compound of Formula (IV) to obtain a compound of Formula (V) is carried out in presence of a transition metal catalyst and a hydrogen source. In some other embodiments, the transition metal catalyst is palladium on carbon, and hydrogen source is hydrogen gas. In some other embodiments, the hydrogenolysis reaction is carried out in presence of a suitable solvent such as dichloromethane, tetrahydrofuran, methanol, ethyl acetate or mixtures thereof. In some embodiments, the hydrogenolysis of a compound of Formula (IV) to obtain a compound of Formula (V) is carried out using 10% palladium on carbon catalyst, in presence of hydrogen gas and in dichloromethane as a solvent.

The compound of Formula (V) is sulfonated by reacting with suitable sulfonating agents in presence of suitable solvent. In some embodiments, compound of Formula (V) is sulfonated by reacting with sulfur trioxide-dimethylformamide complex ($SO_3$-DMF complex) in presence of dimethylformamide as a solvent. This is followed by treatment with tetrabutyl ammonium acetate to obtain a compound of Formula (VI).

The compound of Formula (VI) is converted to a compound of Formula (I) in presence of a suitable reagent. In some embodiments, the compound of Formula (VI) is converted to a compound of Formula (I) by reacting a compound of Formula (VI) with trifluoroacetic acid in suitable solvent such as dichloromethane.

In some embodiments, the compound of Formula (I) is prepared using a process described in Scheme I.

In some embodiments, compound of Formula (I) is further converted to its pharmaceutically acceptable derivative. In some embodiments, compound of Formula (I) is converted to its corresponding sodium salt.

In some embodiments, there is provided a compound of Formula (I) in amorphous form.

In some other embodiments, there is provided a compound of Formula (I) in crystalline form.

In some other embodiments, there is provided a compound of Formula (I) in a crystalline form and having an X-ray powder diffraction pattern comprising a peak selected from the group consisting of 8.08 (±0.2), 11.45 (±0.2), 16.26 (±0.2), 17.89 (±0.2), 18.15 (±0.2), 19.66 (±0.2), 21.15 (±0.2), 23.55 (±0.2), 24.23 (±0.2), 24.94 (±0.2), 25.66 (±0.2) and 29.41 (±0.2) degrees 2 theta.

In some other embodiments, there is provided a compound of Formula (I) in a crystalline form and having an X-ray powder diffraction pattern comprising a peak selected from the group consisting of 16.26 (±0.2), 17.89 (±0.2), 18.15 (±0.2), 19.66 (±0.2), 21.15 (±0.2), 24.94 (±0.2) and 25.66 (±0.2) degrees 2 theta.

Scheme-1

Figure 2:
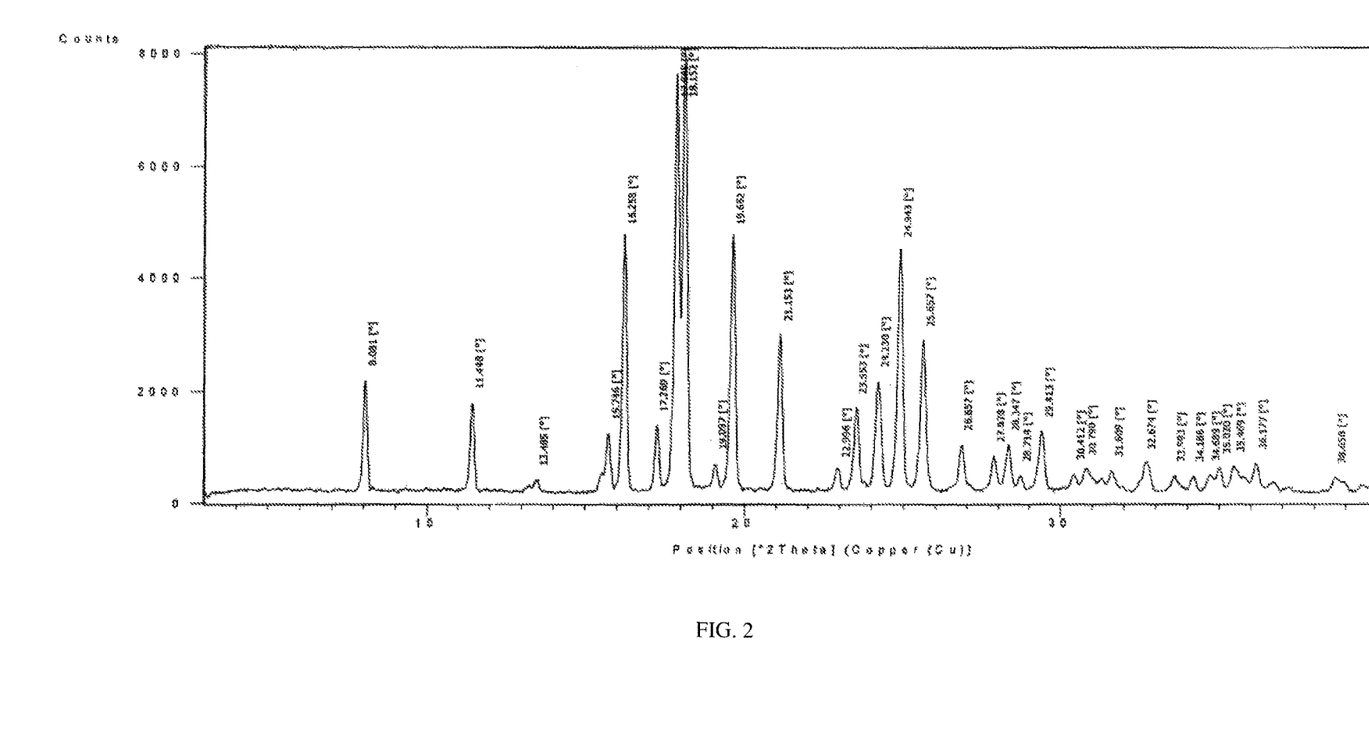
FIG. 2—An X-ray powder diffraction pattern of crystalline form of the compound of Formula (I).

In some embodiments, there is provided a compound of Formula (I) in a crystalline form and having an X-ray powder diffraction pattern substantially the same as shown in FIG. 2.

In some embodiments, there is provided a pharmaceutical composition comprising compound of Formula (I) in crystalline or amorphous form.

In some embodiments, there is provided a process for the preparation of a compound of Formula (III), comprising:

Formula (III)

(a) reacting (2S)-pyrrolidine-2-carboxylic acid (L-proline) with bi-tert-butyl dicarbonate in presence of base to obtain a compound of Formula (VII);

L-Proline

Formula (VII)

(b) reacting a compound of Formula (VII) with ethylchloroformate to obtain a compound of Formula (VIII), followed by hydrogenation to obtain a compound of Formula (IX);

Formula (VIII)

Formula (IX)

(c) converting a compound of Formula (IX) to a compound of Formula (X); and

Formula (X)

(d) reacting a compound of Formula (X) with hydrazine hydrate to obtain compound of Formula (III).

In general, L-proline is reacted with bi-tert-butyl dicarbonate in presence of base such as sodium hydroxide to obtain pyrrolidine-1,2-dicarboxylic acid 1-(1,1-dimethylethyl)ester(S) (VII). The compound of Formula (VII) is then reacted with ethylchloroformate in presence of base such as N-methyl morpholine to provide the compound of Formula (VIII). The compound of Formula (VIII), without isolation, is further reacted with sodium borohydrate to obtain N-tert-butoxylcarbonyl-L-prolinol (IX). The compound of Formula (IX) is first reacted with the solution of Diisopropyl azodicarboxylate and triphenylphosphine in suitable solvent under stirring, followed by reaction with N-hydroxy phthalamide to obtain tert-butyl(2S)-2-[[(1,3-dihydro-1,3-dioxo-2H-isoindol-2-yl)oxy]methyl]-pyrrolidine-1-carboxylate (X). The compound of Formula (X) is reacted with hydrazine hydrate in suitable solvent such as dichloromethane to obtain tert-butyl(2S)-2-[(aminooxy)methyl]pyrrolidine-1-carboxylate of Formula (III). A schematic synthesis of a compound of Formula (III) is given in Scheme-2.

In some general aspect, there is provided a substantially pure (2S, 5R)-7-oxo-N-[(2S)-pyrrolidin-2-yl-methyloxy]-6-(sulfooxy)-1,6-diazabicyclo[3.2.1]octane-2-carboxamide.

The term "substantially pure (2S, 5R)-7-oxo-N-[(2S)-pyrrolidin-2-yl-methyloxy]-6-(sulfooxy)-1,6-diazabicyclo [3.2.1]octane-2-carboxamide" as used herein refers to (2S, 5R)-7-oxo-N-[(2S)-pyrrolidin-2-yl-methyloxy]-6-(sulfooxy)-1,6-diazabicyclo[3.2.1]octane-2-carboxamide having one or more of the following specifications:

(i) (2S, 5R)-7-oxo-N-[(2S)-pyrrolidin-2-yl-methyloxy]-6-(sulfooxy)-1,6-diazabicyclo [3.2.1]octane-2-carboxamide having purity of at least 97% as determined by HPLC.

(ii) (2S, 5R)-7-oxo-N-[(2S)-pyrrolidin-2-yl-methyloxy]-6-(sulfooxy)-1,6-diazabicyclo [3.2.1]octane-2-carboxamide having purity of at least 97%, further containing less than 0.5% of (2S, 5R)-7-oxo-N-[(2R)-pyrrolidin-2-yl-methyloxy]-6-(sulfooxy)-1,6-diazabicyclo [3.2.1]octane-2-carboxamide, as determined by HPLC.

(iii) (2S,5R)-7-oxo-N-[(2S)-pyrrolidin-2-yl-methyloxy]-6-(sulfooxy)-1,6-diazabicyclo [3.2.1]octane-2-carboxamide having purity of at least 97%, further containing less than 2% of (2S,5R)-7-oxo-N-[(2S)-pyrrolidin-2-yl-methyloxy]-5-(sulfooxy)amino]-2-piperidinyl]-2-carboxamide, as determined by HPLC.

Scheme 2

In some embodiments, there is provided (2S, 5R)-7-oxo-N-[(2S)-pyrrolidin-2-yl-methyloxy]-6-(sulfooxy)-1,6-diazabicyclo [3.2.1]octane-2-carboxamide having purity of at least 97% as determined by HPLC.

In some embodiments, there is provided (2S, 5R)-7-oxo-N-[(2S)-pyrrolidin-2-yl-methyloxy]-6-(sulfooxy)-1,6-diazabicyclo[3.2.1]octane-2-carboxamide having purity of at least 97%, further containing less than 0.5% of (2S, 5R)-7-oxo-N-[(2R)-pyrrolidin-2-yl-methyloxy]-6-(sulfooxy)-1,6-diazabicyclo[3.2.1]octane-2-carboxamide, as determined by HPLC.

In some embodiments, there is provided (2S, 5R)-7-oxo-N-[(2S)-pyrrolidin-2-yl-methyloxy]-6-(sulfooxy)-1,6-diazabicyclo[3.2.1]octane-2-carboxamide having purity of at least 97%, further containing less than 2% of (2S, 5R)-7-oxo-N-[(2S)-pyrrolidin-2-yl-methyloxy]-5-(sulfooxy)amino]-2-piperidinyl]-2-carboxamide, as determined by HPLC.

In some embodiments, there is provided a process for preparing (2S, 5R)-7-oxo-N-[(2S)-pyrrolidin-2-yl-methyloxy]-6-(sulfooxy)-1,6-diazabicyclo [3.2.1]octane-2-carboxamide having purity of at least 97% as determined by HPLC, said process comprising:

(a) dissolving (2S, 5R)-7-oxo-N-[(2S)-pyrrolidin-2-yl-methyloxy]-6-(sulfooxy)-1,6-diazabicyclo[3.2.1]octane-2-carboxamide in water, (b) adding isopropanol to the solution obtained in step (a), (c) decanting the upper clear water isopropanol layer obtained in step (b) so as to separate it from the separated oil, and (d) recovering crystals of (2S, 5R)-7-oxo-N-[(2S)-pyrrolidin-2-yl-methyloxy]-6-(sulfooxy)-1,6-diazabicyclo [3.2.1]octane-2-carboxamide.

In some embodiments, there is provided (2S, 5R)-7-oxo-N-[(2S)-pyrrolidin-2-yl-methyloxy]-6-(sulfooxy)-1,6-diazabicyclo [3.2.1]octane-2-carboxamide having purity of 98.5% as determined by HPLC.

In some embodiments, there is provided a process for preparation of substantially pure (2S, 5R)-7-oxo-N-[(2S)-pyrrolidin-2-yl-methyloxy]-6-(sulfooxy)-1,6-diazabicyclo [3.2.1]octane-2-carboxamide wherein, the ratio of water to isopropanol varies from 1:3 to 1:8.

In some embodiments, there is provided a process for preparation of substantially pure (2S, 5R)-7-oxo-N-[(2S)-pyrrolidin-2-yl-methyloxy]-6-(sulfooxy)-1,6-diazabicyclo [3.2.1]octane-2-carboxamide wherein, the ratio of water to isopropanol varies from 1:4 to 1:6.

In some embodiments, there is provided a pharmaceutical composition comprising substantially pure (2S, 5R)-7-oxo-N-[(2S)-pyrrolidin-2-yl-methyloxy]-6-(sulfooxy)-1,6-diazabicyclo[3.2.1]octane-2-carboxamide according to the invention.

In some other embodiments, the pharmaceutical compositions according to the invention may further comprise one or more pharmaceutically acceptable excipients.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Synthesis of tert-butyl (2S)-2-[(aminooxy)methyl]pyrrolidine-1-carboxylate

Step 1: Synthesis of 1-(tert-butoxycarbonyl)-(2S)-pyrrolidine-2-carboxylic acid (VII)

To a stirred suspension of (2S)-pyrrolidine-2-carboxylic acid (L-proline) (200 g, 1.73 mol) in 1,4-dioxan and water mixture (1:1, 1000 ml: 1000 ml) was added a solution of sodium hydroxide (138.97 g, 3.47 mol in 740 ml water) over a period of 20 minutes at 0° C. Bi-tert-butyl dicarbonate (415.3 ml, 1.9 mol in 400 ml 1,4-dioxan) was added to the resulting clear solution over a period of 30 minutes, at temperature of about 0-5° C. The reaction mixture was allowed to warm to room temperature and stirred for 16 hours. After completion of the reaction (monitored by thin layer chromatography), the reaction mixture was concentrated to 40% of the initial volume under reduced pressure at 40-50° C. The pH of the residual mixture was adjusted to 2-2.5 using 30% aqueous potassium hydrogen sulphate at 15° C. under continuous stirring. The separated solid was filtered under suction and washed with water (2×400 ml) and dried under reduced pressure (4 mm Hg), to obtain 370 g of 1-(tert-butoxycarbonyl)-(2S)-pyrrolidine-2-carboxylic acid (VII) as white solid.

Analysis:
Mass: 216 (M+1), for Molecular Weight: 215.24 and Molecular Formula: $C_{10}H_{17}NO_4$;
$^1$H NMR (400 MHz, $CDCl_3$): δ 10.60 (s, 1H), 4.35-4.24 (dd, 1H), 3.54-3.34 (M, 2H), 2.27-1.91 (unresolved, 4H), 1.47-1.41 (d, 9H);
Purity as determined by HPLC: 99.92%.

Step 2: Synthesis of tert-butyl-(2S)-2-(hydroxymethyl)-pyrrolidine-1-carboxylate (IX)

N-Methylmorpholine (113 ml, 1.114 mol) was added to the suspension of 1-(tert-butoxycarbonyl)-(2S)-pyrrolidine-2-carboxylic acid (VII, 30 g, 139 mmol) in tetrahydrofuran (2000 ml) under stirring at temperature of about 0° C. Ethyl chloroformate (106 ml, 1.114 mol) was added drop-wise to the above obtained clear solution over a period of 30 minutes. After stirring for 1 hour, the resulting suspension was filtered over celite and the residue was washed with tetrahydrofuran (2×200 ml). To the combined filtrate was added dropwise a solution of sodium borohydride (42.1 g, 1.114 mol) in 210 ml water, containing a catalytic amount of sodium hydroxide, at temperature of about −10° C. over a period of 1-2 hours under stirring. The reaction mixture was allowed to warm to room temperature and stirred further for an hour. The reaction mixture was filtered through celite bed and the filtrate concentrated under reduced pressure to yield 180 g of tert-butyl(2S)-2-(hydroxymethyl)-pyrrolidene-1-carboxylate (IX) as colorless oil.

Analysis:
Mass: 202 (M+1), for Molecular Weight: 201.2 and Molecular Formula: $C_{10}H_{19}NO_3$;
$^1$H NMR (400 MHz, $CDCl_3$): δ 3.94-3.92 (m, 1H), 3.80 (board, 1H), 3.63-3.54 (m, 2H), 3.45-3.40 (m, 1H), 3.32-3.28 (m, 1H), 2.01-1.96 (m, 1H), 1.84-1.75 (m, 2H), 1.63 (m, 1H), 1.45 (s, 9H);
Purity as determined by HPLC: 87.7%.

Step 3: Synthesis of tert-butyl (2S)-2-[[(1,3-dihydro-1,3-dioxo-2H-isoindol-2-yl)oxy]methyl]-pyrrolidine-1-carboxylate (X)

Triphenylphosphine (328.4 g, 1.253 mol) in tetrahydrofuran (1260 ml) was added to solution of Diisopropyl azodicarboxylate (253.3 g, 1.253 mol) in tetrahydrofuran at temperature of −15° C. under stirring. After stirring for an hour, N-tert-butoxylcarbonyl-L-prolinol (IX) (180 g, 0.895 mol) in tetrahydrofuran (540 ml) was added to the resulting mixture over a period of 15 minutes. After stirring the mixture for 45 minutes, N-Hydroxy phthalimide (146 g, 0.895 mol) was added and the mixture was allowed to warm to room temperature and stirred further for 16 hours. The solvent was evaporated under reduced pressure and residual oil was dissolved in dichloromethane (5000 ml) and washed with an aqueous 5% sodium hydrogen carbonate solution (2×300 ml). The organic layer was dried over anhydrous sodium sulfate and the solvent evaporated under reduced pressure to obtain viscous oil. Diisopropyl ether (720 ml) was added to the oil, the mixture was stirred well and separated solid was filtered under suction. The filtrate was concentrated under reduced pressure and the residue was further purified by chromatography over a silica gel column (60-120 mesh) and eluted with mixtures of ethyl acetate and hexane. Upon concentration of the combined eluted fractions, 230 g of tert-butyl (2S)-2-[[(1,3-dihydro-1,3-dioxo-2H-isoindol-2-yl)oxy]methyl]-pyrrolidine-1-carboxylate (X) was obtained as yellow oil.

Analysis:
Mass: 347.3 (M+1), for Molecular Weight: 346.39 and Molecular Formula: $C_{18}H_{22}N_2O_5$;
$^1$H NMR (400 MHz, $CDCl_3$): δ 7.80-7.78 (m, 2H), 7.72-7.70 (m, 2H), 4.32 (brs, 1H), 4.05 (brs, 2H), 3.36-3.31 (m, 2H), 2.27-2.25 (m, 1H), 2.08 (m, 1H), 1.88-1.87 (m, 2H), 1.43 (s, 9H).

Step 4: Synthesis of tert-butyl (2S)-2-[(aminooxy)methyl]pyrrolidine-1-carboxylate (III)

To a stirred solution of the compound of Formula (X) (100 g, 0.288 mol) in dichloromethane (2000 ml) was added 99% hydrazine hydrate (28.9 g, 0.577 mol) drop-wise over a period of 30 minutes at temperature of about 25° C. The stirring was continued further for a period of 3 hours. The separated solid was filtered and the solid washed with additional dichloromethane (2×500 ml). The combined organic layer was collected and washed with water (2×500 ml). The organic layer was dried over anhydrous sodium sulfate and concentrated under reduced pressure to obtain 62.4 g of tert-butyl (2S)-2-[(aminooxy)methyl]pyrrolidine-1-carboxylate (III) as a colorless oil. This was used as such for the next reaction without further purification.

Analysis:
Mass: 215.1 (M−1), for Molecular Weight: 216.2 and Molecular Formula: $C_{10}H_{20}N_2O_3$.

Example 2

Synthesis of (2S,5R)-7-oxo-N-[(2S)-pyrrolidin-2-ylmethyloxy]-6-(sulfooxy)-1,6-diazabicyclo[3.2.1]octane-2-carboxamide (I)

Step 1: Synthesis of tert-butyl (2S)-2-{[({[2S,5R)-6-(benzyloxy)-7-oxo-1,6-diazabicylco[3.2.1]oct-2-yl]carbonyl}amino)oxy]methyl}pyrrolidine-1-carboxylate (IV)

Sodium(2S,5R)-6-(benzyloxy)-7-oxo-1,6-diazabicyclo[3.2.1]octane-2-carboxylate (II, 77.4 g, 0.259 mol; prepared according to the procedure disclosed in Indian patent application No. 699/MUM/2013) was dissolved in water (774 ml) to obtain a clear solution. To the clear solution was added EDC.HCl (120.8 g, 0.632 mol) at temperature of about 15° C. and after 10 minutes a solution of tert-butyl (2S)-2-[(aminooxy)methyl]pyrrolidine-1-carboxylate (III, 62.4 g, 0.288 moles prepared as per the literature procedure depicted in scheme 2) in dimethylformamide (125 ml) was added drop wise under continuous stirring at temperature of about 10° C. The reaction mass was allowed to warm to temperature of about 25° C. and then HOBt (38.96 g, 0.288 mol) was added in small portions over a period of 15 minutes and the resulting mixture was further stirred at room temperature for 16 hours. The reaction progress was monitored using thin layer chromatography using mixture of acetone and hexane (35:65) as solvent system. The resulting suspension was filtered and the residue was washed with water (200 ml). The residual white solid was suspended in water (200 ml) and the mixture stirred with heating at temperature of about 50° C. for 3 hours. The resulting suspension was filtered, the residue dried at atmospheric temperature and then dried under vacuum to obtain 105 g of tert-Butyl(2S)-2-{[({[2S,5R)-6-(benzyloxy)-7-oxo-1,6-diazabicylco[3.2.1]oct-2-yl]carbonyl}amino)oxy] methyl}pyrolidine-1-carboxylate (IV) as off white solid.

Analysis:

Mass: 475.4 (M+1), for Molecular Weight of 474.56 and Molecular Formula of $C_{24}H_{34}N_4O_6$;

$^1$H NMR (400 MHz, CDCl$_3$): δ 10.16 (br s, 1H), 7.43-7.35 (m, 5H), 5.06-4.88 (dd, 2H), 4.12 (s, 1H), 3.94-3.93 (d, 2H), 3.83 (unresolved s, 1H), 3.75-3.73 (m, 1H), 3.37-3.28 (dt, 2H), 3.02-2.86 (dd, 2H), 2.31-2.26 (m, 1H), 2.02-1.84 (m, 6H), 1.71-1.68 (m, 1H), 1.45 (s, 9H).

Step 2: Synthesis of tert-butyl(2S)-2-{[({[2S,5R)-6-hydroxy-7-oxo-1,6-diazabicylco[3.2.1]oct-2-yl] carbonyl}amino)oxy]methyl}pyrrolidine-1-carboxylate (V)

tert-butyl(2S)-2-{[({[2S,5R)-6-(benzyloxy)-7-oxo-1,6-diazabicylco[3.2.1]oct-2-yl]carbonyl}amino)oxy] methyl}pyrrolidine-1-carboxylate (IV, 85 g, 0.179 mol) was dissolved in a mixture of dimethylformamide and dichloromethane (1:1, 425 ml: 425 ml) to obtain a clear solution. To this solution was added 10% Pd—C (17 g, 50% wet) catalyst. The suspension was stirred for 4 hours under 7 psi hydrogen atmosphere at temperature of about 25° C. The resulting mixture was filtered through celite under suction. The residue was washed with dichloromethane (170 ml). The solvent from the filtrate was evaporated under reduced pressure to furnish 68.8 g of tert-butyl(2S)-2-{[({[2S,5R)-6-hydroxy-7-oxo-1,6-diazabicylco[3.2.1]oct-2-yl]carbonyl} amino)oxy]methyl}pyrrolidine-1-carboxylate (V) as oil. The obtained product was used as such for the next reaction without further purification.

Analysis:

Mass: 385.4 (M+1), for Molecular Weight of 384.4 and Molecular Formula of $C_{17}H_{28}N_4O_6$.

Step 3: Synthesis of tert-butyl(2S)-2-{[({[2S,5R)-6-(sulfooxy)-7-oxo-1,6-diazabicylco[3.2.1]oct-2-yl] carbonyl}amino)oxy]methyl}pyrolidine-1-carboxylate, tetra butyl ammonium salt (VI)

To solution of tert-butyl(2S)-2-{[({[2S,5R)-6-hydroxy7-oxo-1,6-diazabicylco [3.2.1]oct-2-yl]carbonyl}amino)oxy] methyl}pyrrolidine-1-carboxylate (V, 68.8 g, 0.178 mol) in dimethylformamide, (345 ml) was added sulfur trioxide dimethylformamide complex (30 g, 0.196 mol) under stirring at temperature of about 10° C. The reaction mass was stirred at the same temperature for 30 minutes and then allowed to warm to room temperature. After 2 hours solution of tetra butyl ammonium acetate (59.09 g, 0.196 mol) in water (178 ml) was added to the reaction mixture under stirring. After 2 hours, the solvent from the reaction mixture was evaporated under reduced pressure to obtain an oily residue. The oily mass was co-evaporated with xylene (2×140 ml) to obtain thick mass. This mass was partitioned between dichloromethane (690 ml) and water (690 ml). The organic layer was separated and the aqueous layer re-extracted with dichloromethane (345 ml). The combined organic extracts were washed with water (3×345 ml) and dried over anhydrous sodium sulfate. The solvent was evaporated under reduced pressure and the resulting oily mass was triturated with ether (3×140 ml), each time the ether layer was decanted and finally the residue was concentrated under reduced pressure to obtain 102 g of tert-butyl(2S)-2-{[({[2S,5R)-6-(sulfooxy)-7-oxo-1,6-diazabicylco[3.2.1]oct-2-yl]carbonyl}amino)oxy] methyl}pyrrolidine-1-carboxylate, tetrabutyl ammonium salt (VI) as fluffy material.

Analysis:

Mass: 463.4 (M−1 without TBA), for Molecular Weight of 705.96 and Molecular Formula of $C_{33}H_{63}N_5O_9S$;

$^1$H NMR (400 MHz, CDCl$_3$): δ 10.2 (s, 1H), 4.35 (s, 1H), 4.14 (s, 1H), 3.91-3.92 (d, 2H), 3.74 (m, 1H), 3.36-3.27 (m, 10H), 2.96-2.88 (dd, 2H), 2.31-2.26 (m, 2H), 2.19-1.98 (m, 2H), 1.95-1.70 (m, 4H), 1.68-1.62 (p, 8H), 1.49-1.40 (m, 17H), 1.02-0.98 (t, 12H).

Figure 1:
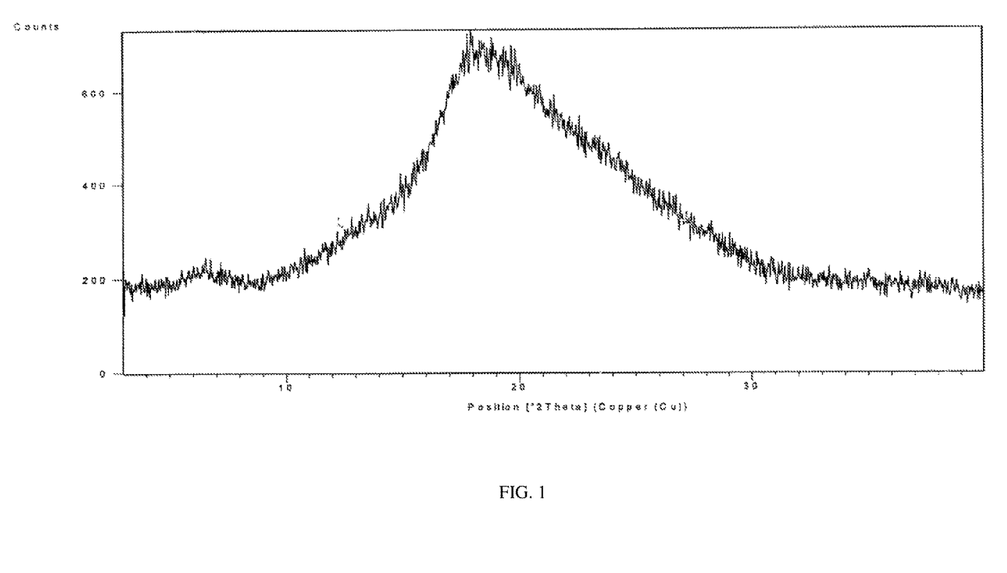
FIG. 1—An X-ray powder diffraction pattern of amorphous form of the compound of Formula (I).

Step 4: (2S,5R)-7-oxo-N-[(2S)-pyrrolidin-2-yl-methyloxy]-6-(sulfooxy)-1,6-diaza bicyclo [3.2.1] octane-2-carboxamide (I)

tert-butyl(2S)-2-{[({[2S,5R)-6-(sulfooxy)-7-oxo-1,6-diazabicylco[3.2.1]oct-2-yl]carbonyl}amino)oxy] methyl}pyrrolidine-1-carboxylate, tetrabutylammonium salt (VI) (50 g, 0.0708 mol) was dissolved in dichloromethane (250 ml) and to the clear solution was slowly added trifluoroacetic acid (250 ml) at temperature of about −10° C. over a period of 1 hour under stirring. After stirring for an hour, the resulting mixture was poured into hexane (2500 ml) and the oily layer was separated. This procedure was repeated one more time and finally the separated oily layer was added to diethyl ether (500 ml) under vigorous stirring at temperature of about 25° C. The ether layer was removed by decantation from the precipitated solid. This procedure was repeated twice again with diethyl ether (2×500 ml). The solid thus obtained was stirred with fresh dichloromethane (500 ml) for 30 minutes and filtered. The residual solid was dried at temperature of about 45° C. under reduced pressure to yield 25 g of (2S,5R)-7-Oxo-N-[(2S)-pyrrolidin-2-yl-methyloxy]-6-(sulfooxy)-1,6-diazabicyclo [3.2.1]octane-2-carboxamide (I) in amorphous form. The XRD of the obtained amorphous form is shown in FIG. 1.

Analysis:

Mass: 363.2 (M−1), for Molecular Weight: 364.37 and Molecular Formula: $C_{12}H_{20}N_4O_7S$;

$^1$H NMR (400 MHz, DMSO-D$_6$): δ 11.73 (s, 1H), 8.62-8.83 (d, 2H), 3.88-4.00 (m, 3H), 3.74-3.81 (m, 2H), 3.19 (t, 2H), 2.94-3.04 (dd, 2H), 1.96-2.03 (m, 2H), 1.80-1.92 (m, 3H), 1.54-1.73 (m, 3H);

Purity as determined by HPLC: 90.30%.

Example 3

Preparation of Crystalline Form I of (2S,5R)-7-oxo-N-[(2S)-pyrrolidin-2-yl-methyloxy]-6-(sulfooxy)-1,6-diaza bicyclo[3.2.1]octane-2-carboxamide The amorphous solid obtained in the Step 4 of Example 2 was dissolved in water (75 ml) and to this solution isopropanol (200 ml) was slowly added at temperature of about 25° C. The solution was further stirred for 12 hours. The separated solid thus obtained was filtered and washed with additional isopropanol (25 ml) and dried under reduced pressure to obtain 19 g of (2S,5R)-7-Oxo-N-[(2S)-pyrrolidin-2-yl-methyloxy]-6-(sulfooxy)-1,6-diazabicyclo[3.2.1]octane-2-carboxamide as crystalline Form I. The XRD of the obtained crystalline Form I is shown in FIG. 2.

X-ray powder diffraction pattern comprising peak at (2 Theta Values): 8.08 (±0.2), 11.45 (±0.2), 16.26 (±0.2), 17.89 (±0.2), 18.15 (±0.2), 19.66 (±0.2), 21.15 (±0.2), 23.55 (±0.2), 24.23 (±0.2), 24.94 (±0.2), 25.66 (±0.2) and 29.41 (±0.2).

Typical X-ray analysis was performed as follows. Pass the test substance through sieve #100 BSS or gently grind it with a mortar and pestle. Place the test substance uniformly on a sample holder having cavity surface on one side, press the sample and cut into thin uniform film using a glass slide in such a way that the surface of the sample should be smooth and even. Record the X-ray diffractogram using the following instrument parameters:

Instrument: X-Ray Diffractometer
(PANalytical, Model X'Pert Pro MPD)
Target source: CuK($\alpha$)
Antiscattering slit (Incident beam): 1°
Programmable Divergent slit: 10 mm (fixed)
Anti-scattering slit (Diffracted beam): 5.5 mm
Step width: 0.02°
Voltage: 40 kV
Current: 40 mA
Time per step: 30 seconds
Scan range: 3 to 40°

Example 4

Preparation of Pure (2S,5R)-7-oxo-N-[(2S)-pyrrolidin-2-yl-methyloxy]-6-(sulfooxy)-1,6-diazabicyclo[3.2.1]octane-2-carboxamide (2S,5R)-7-Oxo-N-[(2S)-pyrrolidin-2-yl-methyloxy]-6-(sulfooxy)-1,6-diazabicyclo [3.2.1]octane-2-carboxamide (5 g) was slowly dissolved in water (50 ml) under stirring until clear solution appears. To this clear solution 350 ml of isopropanol was added drop wise under stirring over the period of 2 hours. Formation of fine white precipitates was observed after the completion of the addition of isopropanol. The resulted fine suspension was stirred at temperature of about 25° C. for 20 hours. The formed white precipitates were filtered and vacuum dried at temperature of about 30-40° C., under reduced pressure (2 mm Hg) to get 4.4 g of (2S,5R)-7-oxo-N-[(2S)-pyrrolidin-2-yl-methyloxy]-6-(sulfooxy)-1,6-diazabicyclo [3.2.1]octane-2-carboxamide.

The above obtained (2S,5R)-7-oxo-N-[(2S)-pyrrolidin-2-yl-methyloxy]-6-(sulfooxy)-1,6-diazabicyclo[3.2.1]octane-2-carboxamide (3.4 gm) was dissolved in 34 ml of water to get clear solution. To the obtained clear solution 170 ml of isopropanol was added drop wise over a period of 1 hour. Formation of fine oily globules was observed and allowed to stand still for 15 minutes. The upper clear water and isopropanol layer was decanted from the oily mass. The clear decanted solution was allowed to stand at temperature of about 25° C. for 48 hours. Formation of crystals was observed and were collected by filtration. The collected crystals were dried at temperature of about 30-40° C., under reduced pressure (2 mm Hg) to get 2 g of (2S,5R)-7-oxo-N-[(2S)-pyrrolidin-2-yl-methyloxy]-6-(sulfooxy)-1,6-diazabicyclo [3.2.1]octane-2-carboxamide which was analyzed for content of various components using HPLC and the results are described in Table 1.

The relative % content of (2S,5R)-7-oxo-N-[(2S)-pyrrolidin-2-yl-methyloxy]-6-(sulfooxy)-1,6-diazabicyclo[3.2.1]octane-2-carboxamide with other substances (Table 1) was determined using HPLC (Agilent 1100 or equivalent). The HPLC column having 250 mm length and 4.6 mm ID packed with 5$\mu$ particles of octa-decyl silane (ODS) was used. Mobile phase A used was a mixture of buffer (0.02 M potassium dihydrogen phosphate in HPLC grade water, pH adjusted to 2.5 with orthophosphoric acid and again readjusted to 7.0 with dilute ammonia), HPLC grade water and acetonitrile in a ratio of 40:60:0.2; v/v/v. Mobile phase B was mixture of buffer and acetonitrile in a ratio of 40:60; v/v. Mobile phase was run in gradient mode. Initially mobile phase A and B was run at 100:0 for 15 minutes, slowly ratio of mobile phase B was raised to 100% in 10 minutes, held for 10 minutes at this concentration and brought back to initial condition in next 5 minutes and held for 10 minutes before next run. Flow rate of mobile phase was maintained at 1.0 ml/min Column temperature was maintained at temperature of about 30° C. Detection was carried out using UV detector at wavelength 225 nm. Test solutions were prepared in mobile phase A. The method is capable of resolving diastereomers (Table 1, Sr. No. 1 and 2) with resolution of not less than 2.0.

TABLE 1

Results of HPLC analysis of (2S,5R)-7-oxo-N-[(2S)-pyrrolidin-2-yl-methyloxy]-6-(sulfooxy)-1,6-diazabicyclo[3.2.1]octane-2-carboxamide according to the invention

| Sr. | Component | Relative % (as determined by HPLC) |
|---|---|---|
| 1 | (2S,5R)-7-Oxo-N-[(2S)-pyrrolidin-2-yl-methyloxy]-6-(sulfooxy)-1,6-diazabicyclo[3.2.1]octane-2-carboxamide | 98.5% |
| 2 | (2S,5R)-7-Oxo-N-[(2R)-pyrrolidin-2-yl-methyloxy]-6-(sulfooxy)-1,6-diazabicyclo[3.2.1]octane-2-carboxamide | Less than 0.5% |
| 3 | (2S,5R)-N-[[(2S)-pyrrolidin-2-yl-methyloxy]-[5-(sulfooxy)amino]-2-piperidinyl]-2-carboxamide | Less than 1.0% |

The invention claimed is:
1. A process for preparation of a compound of Formula (I) in a crystalline form, comprising:

Formula (I)

(a) reacting a compound of Formula (II) with a compound of Formula (III) to obtain a compound of Formula (IV);

(b) hydrogenolysis of a compound of Formula (IV) to obtain a compound of Formula (V);

(C) sulfonating a compound of Formula (V), followed by tetrabutylammonium salt formation to obtain a compound of Formula (VI); and

(d) reacting the compound of Formula (VI) with trifluoroacetic acid to obtain a compound of Formula (I);
(e) dissolving the compound of Formula (I) obtained in step-(d) in water to obtain a solution;
(f) adding isopropanol to the solution obtained in step-(e); and
(g) isolating a compound of Formula (I) in crystalline form.

2. The process according to claim 1, wherein compound of Formula (IV) is obtained by reacting a compound of Formula (II) with a compound of Formula (III) in presence of 1-hydroxybenzotriazole and 1-ethyl-3-(3-dimethylamino propyl)carbodiimide hydrochloride.

3. The process according to claim 1, wherein compound of Formula (IV) is obtained by reacting a compound of Formula (II) with a compound of Formula (III) in presence of mixture of water and dimethylformamide as solvent.

4. The process according to claim 1, wherein compound of Formula (VI) is obtained by sulfonating a compound of Formula (V) with sulfur trioxide-dimethylformamide complex, followed by treatment with tetrabutyl ammonium acetate.

5. A compound of Formula (I) in a crystalline form having an X-ray powder diffraction pattern comprising a peak selected from 16.26 (±0.2), 17.89 (±0.2), 18.15 (±0.2), 19.66 (±0.2), 21.15 (±0.2), 24.94 (±0.2) or 25.66 (±0.2) degrees 2 theta wherein the compound of Formula (I) is 6. The compound of Formula (I) according to claim 5, having an X-ray powder diffraction pattern comprising a peak selected from the group consisting of 8.08 (±0.2), 11.45 (±0.2), 16.26 (±0.2), 17.89 (±0.2), 18.15 (±0.2), 19.66 (±0.2), 21.15 (±0.2), 23.55 (±0.2), 24.23 (±0.2), 24.94 (±0.2), 25.66 (±0.2) and 29.41 (±0.2) degrees 2 theta.

7. The process according to claim 1, wherein the compound of Formula (I) is having a purity of at least 97%, wherein the process comprising:
(a) dissolving compound of Formula (I) obtained in claim 1 in water,
(b) adding isopropanol to the solution obtained in step (a),
(c) decanting the upper clear water isopropanol layer obtained in step (b) so as to separate it from the separated oil, and
(d) recovering crystals of the compound of Formula (I).

8. A pharmaceutical composition comprising: the compound according to claim 5 or 6; and one or more pharmaceutically acceptable excipients.

* * * * *